US011464576B2

(12) United States Patent
Klein et al.

(10) Patent No.: US 11,464,576 B2
(45) Date of Patent: Oct. 11, 2022

(54) SYSTEM AND METHOD FOR DISPLAYING AN ALIGNMENT CT

(71) Applicant: Covidien LP, Mansfield, MA (US)

(72) Inventors: Eyal Klein, Herzliya (IL); Oren P. Weingarten, Herzliya (IL)

(73) Assignee: COVIDIEN LP, Mansfield, MA (US)

( * ) Notice: Subject to any disclaimer, the term of this patent is extended or adjusted under 35 U.S.C. 154(b) by 314 days.

(21) Appl. No.: 16/264,817

(22) Filed: Feb. 1, 2019

(65) Prior Publication Data

US 2019/0247125 A1 Aug. 15, 2019

Related U.S. Application Data

(60) Provisional application No. 62/628,560, filed on Feb. 9, 2018.

(51) Int. Cl.
*A61B 34/20* (2016.01)
*A61B 1/267* (2006.01)
(Continued)

(52) U.S. Cl.
CPC .............. *A61B 34/20* (2016.02); *A61B 34/25* (2016.02); *A61B 90/37* (2016.02); *G06T 15/00* (2013.01);
(Continued)

(58) Field of Classification Search
CPC .................... A61B 34/20; A61B 90/37; A61B 2017/00809; A61B 2034/107;
(Continued)

(56) References Cited

U.S. PATENT DOCUMENTS 5,227,985 A 7/1993 DeMenthon
5,237,647 A 8/1993 Roberts et al.
(Continued)

FOREIGN PATENT DOCUMENTS

DE 102009007360 A1 8/2010
JP 2001518351 A 10/2001
(Continued)

OTHER PUBLICATIONS

Extended European Search Report issued in corresponding Appl. No. EP 19156249.5 dated Jul. 8, 2019 (8 pages).
(Continued)

*Primary Examiner* — Jason M Ip
(74) *Attorney, Agent, or Firm* — Weber Rosselli & Cannon LLP

(57) ABSTRACT

A system for navigating to a catheter to a target is disclosed. The system includes a probe and a workstation. The probe is configured to be navigated through a patient's airways and includes a location sensor. The workstation is in operative communication with the probe. The workstation includes a memory and at least one processor. The memory stores a navigation plan and a program that, when executed by the processor, is configured to generate a 3D rendering of the patient's airways, generate a view using the 3D rendering, and display the view featuring at least a portion of the navigation plan. Generating the view includes executing a first transfer function for a first range from a distal tip of the location sensor and executing a second transfer function for a second range from the distal tip of the location sensor.

20 Claims, 4 Drawing Sheets

(51) Int. Cl.
  *A61B 90/00* (2016.01)
  *A61B 34/00* (2016.01)
  *G06T 15/00* (2011.01)
  *A61B 34/10* (2016.01)
  *A61M 25/01* (2006.01)
  *A61B 1/018* (2006.01)
  *A61B 10/02* (2006.01)
  *A61B 17/00* (2006.01)

(52) U.S. Cl.
  CPC ............ *A61B 1/018* (2013.01); *A61B 1/2676* (2013.01); *A61B 10/02* (2013.01); *A61B 2017/00809* (2013.01); *A61B 2034/107* (2016.02); *A61B 2034/2051* (2016.02); *A61B 2034/2055* (2016.02); *A61B 2034/2061* (2016.02); *A61B 2034/2065* (2016.02); *A61B 2034/2068* (2016.02); *A61B 2034/2072* (2016.02); *A61B 2090/367* (2016.02); *A61B 2090/3925* (2016.02); *A61M 2025/0166* (2013.01)

(58) Field of Classification Search
  CPC ...... A61B 2034/2051; A61B 2090/367; A61B 1/2676; G06T 15/00
  See application file for complete search history.

(56) References Cited

U.S. PATENT DOCUMENTS

| | | |
|---|---|---|
| 5,297,061 A | 3/1994 | Dementhon et al. |
| 5,364,392 A | 11/1994 | Warner et al. |
| 5,685,839 A | 11/1997 | Edwards et al. |
| 5,995,107 A | 11/1999 | Berteig et al. |
| 6,188,355 B1 | 2/2001 | Gilboa |
| 6,262,734 B1 | 7/2001 | Ishikawa |
| 6,346,938 B1 | 2/2002 | Chan et al. |
| 6,373,916 B1 | 4/2002 | Inoue et al. |
| 6,427,089 B1 | 7/2002 | Knowlton |
| 6,473,634 B1 | 10/2002 | Barni |
| 6,575,969 B1 | 6/2003 | Rittman, III et al. |
| 6,689,127 B1 | 2/2004 | Gough et al. |
| 7,113,832 B2 | 9/2006 | Longo |
| 7,233,820 B2 | 6/2007 | Gilboa |
| 7,551,759 B2 | 6/2009 | Hristov et al. |
| 7,822,461 B2 | 10/2010 | Geiger et al. |
| 7,916,918 B2 | 3/2011 | Suri et al. |
| 8,150,111 B2 | 4/2012 | Borland et al. |
| 8,482,606 B2 | 7/2013 | Razzaque et al. |
| 8,585,598 B2 | 11/2013 | Razzaque et al. |
| 8,625,869 B2 | 1/2014 | Harder et al. |
| 8,641,621 B2 | 2/2014 | Razzaque et al. |
| 8,700,132 B2 | 4/2014 | Ganatra et al. |
| 8,821,376 B2 | 9/2014 | Tolkowsky |
| 9,226,687 B2 | 1/2016 | Soper et al. |
| 9,433,390 B2 | 9/2016 | Nathaniel et al. |
| 9,459,770 B2 | 10/2016 | Baker |
| 9,530,219 B2 | 12/2016 | Markov et al. |
| 9,603,668 B2 | 3/2017 | Weingarten et al. |
| 9,633,431 B2 | 4/2017 | Merlet |
| 9,639,666 B2 | 5/2017 | Baker |
| 9,727,986 B2 | 8/2017 | Greenburg |
| 9,754,367 B2 | 9/2017 | Lachmanovich et al. |
| 9,833,167 B2 | 12/2017 | Cohen et al. |
| 9,836,848 B2 | 12/2017 | Markov et al. |
| 9,888,898 B2 | 2/2018 | Imagawa et al. |
| 9,925,009 B2 | 3/2018 | Baker |
| 10,127,629 B2 | 11/2018 | Razzaque et al. |
| 10,130,316 B2 | 11/2018 | Funabasama et al. |
| 10,159,447 B2 | 12/2018 | Klein et al. |
| 10,674,970 B2 | 6/2020 | Averbuch et al. |
| 10,896,506 B2 | 1/2021 | Zhao et al. |
| 2002/0026187 A1 | 2/2002 | Swanson |
| 2002/0193677 A1 | 12/2002 | Thornton |
| 2004/0049254 A1 | 3/2004 | Longo |
| 2005/0080333 A1 | 4/2005 | Piron et al. |
| 2005/0107679 A1* | 5/2005 | Geiger .................. G06T 19/003 600/407 |
| 2005/0245920 A1 | 11/2005 | Vitullo et al. |
| 2006/0004351 A1 | 1/2006 | Arless et al. |
| 2006/0033728 A1 | 2/2006 | Sako |
| 2006/0116576 A1* | 6/2006 | McGee .................. A61B 6/547 600/434 |
| 2006/0235671 A1 | 10/2006 | Kirchberg et al. |
| 2006/0239400 A1 | 10/2006 | Sukovic et al. |
| 2007/0167714 A1 | 7/2007 | Kiraly et al. |
| 2007/0238981 A1* | 10/2007 | Zhu ........................ A61B 34/20 600/424 |
| 2007/0257903 A1 | 11/2007 | Gutierrez et al. |
| 2007/0288207 A1 | 12/2007 | Backe |
| 2008/0033424 A1 | 2/2008 | van der Weide et al. |
| 2009/0003668 A1 | 1/2009 | Matsumoto |
| 2009/0012390 A1 | 1/2009 | Pescatore et al. |
| 2009/0030306 A1 | 1/2009 | Miyoshi et al. |
| 2009/0099452 A1 | 4/2009 | Hashimoto |
| 2010/0312094 A1 | 12/2010 | Guttman et al. |
| 2011/0118723 A1 | 5/2011 | Turner et al. |
| 2011/0234780 A1 | 9/2011 | Ito et al. |
| 2011/0237897 A1 | 9/2011 | Gilboa |
| 2012/0059248 A1 | 3/2012 | Holsing et al. |
| 2012/0259204 A1 | 10/2012 | Carrat |
| 2012/0259326 A1 | 10/2012 | Brannan et al. |
| 2013/0165854 A1 | 6/2013 | Sandhu et al. |
| 2013/0197357 A1 | 8/2013 | Green et al. |
| 2013/0223702 A1 | 8/2013 | Holsing et al. |
| 2013/0225942 A1 | 8/2013 | Holsing et al. |
| 2013/0281838 A1 | 10/2013 | Trumer et al. |
| 2014/0051986 A1 | 2/2014 | Zhao et al. |
| 2014/0088457 A1 | 3/2014 | Johnson |
| 2014/0135744 A1 | 5/2014 | Stein et al. |
| 2014/0187949 A1 | 7/2014 | Zhao et al. |
| 2014/0267031 A1 | 9/2014 | Huebner |
| 2014/0276005 A1 | 9/2014 | Forsyth |
| 2014/0276033 A1 | 9/2014 | Brannan et al. |
| 2014/0282216 A1 | 9/2014 | Baker |
| 2014/0359535 A1 | 12/2014 | Little |
| 2015/0141809 A1 | 5/2015 | Costello et al. |
| 2015/0265257 A1 | 9/2015 | Costello et al. |
| 2015/0305650 A1 | 10/2015 | Hunter et al. |
| 2016/0000303 A1 | 1/2016 | Klein et al. |
| 2016/0000356 A1 | 1/2016 | Brown et al. |
| 2016/0000414 A1 | 1/2016 | Brown et al. |
| 2016/0000517 A1 | 1/2016 | Kehat et al. |
| 2016/0000520 A1 | 1/2016 | Lachmanovich et al. |
| 2016/0005220 A1* | 1/2016 | Weingarten ........... G06T 7/0012 382/131 |
| 2017/0084027 A1 | 3/2017 | Mintz et al. |
| 2018/0008212 A1 | 1/2018 | Brown et al. |

FOREIGN PATENT DOCUMENTS

| | | |
|---|---|---|
| JP | 2006198107 A | 8/2006 |
| JP | 2008054763 A | 3/2008 |
| JP | 2011516184 A | 5/2011 |
| JP | 2012187405 A | 10/2012 |
| WO | 0010456 A1 | 3/2000 |
| WO | 0167035 A1 | 9/2001 |
| WO | 2008095068 A1 | 8/2008 |
| WO | 2011063061 A2 | 5/2011 |
| WO | 2012071388 A2 | 5/2012 |
| WO | 2013080131 A1 | 6/2013 |
| WO | 2014025551 A1 | 2/2014 |

OTHER PUBLICATIONS

Extended European Search report for application No. 15815034.2 dated Mar. 8, 2018, 7 pages.
Japanese Office Action corresponding to counterpart Patent Application JP 2016-575371 dated Mar. 1, 2019.
Australian Examination Report No. 1 corresponding to counterpart Patent Application 2015283938 dated Mar. 15, 2019.

(56) References Cited

OTHER PUBLICATIONS

Chinese First Office Action corresponding to counterpart Patent Application No. CN 201580043916.8 dated Mar. 26, 2019.

* cited by examiner

SYSTEM AND METHOD FOR DISPLAYING AN ALIGNMENT CT

CROSS-REFERENCE TO RELATED APPLICATIONS

This application claims the benefit of the filing date of provisional U.S. Patent Application No. 62/628,560, filed Feb. 9, 2018, the entire contents of which are incorporated herein by reference.

BACKGROUND

Visualization techniques related to visualizing a patient's lungs have been developed so as to help clinicians perform diagnoses and/or surgeries on the patient's lungs. Visualization is especially important for identifying a location of a diseased region. Further, when treating the diseased region, additional emphasis is given to identification of the particular location of the diseased region so that a surgical operation is performed at the correct location.

SUMMARY

The disclosure is directed to a system for navigating a surgical device to a target. The system includes a probe, which includes a location sensor, configured to be navigated through a patient's airways. The system further includes a workstation in operative communication with the probe. The workstation includes a memory and at least one processor. The memory stores a navigation plan and a program that, when executed by the processor, is configured to generate a three-dimensional (3D) rendering of the patient's airways, generate a view using the 3D rendering, and present a user interface that guides a user through the navigation plan, the user interface configured to display the 3D view. To generate the view, the processor executes a first transfer function for a first range from the location sensor to generate one or more airways within the 3D rendering and executes a second transfer function for a second range from the location sensor to generate the one or more targets within the 3D rendering. One or more targets include one or more lesions.

In an aspect, the first transfer function is executed using a first voxel density, and the second transfer function is executed using a second voxel density. The first and second ranges may include various distances and relationships between the ranges and may be determined at various times and in varying manners. For example, the first range may be less than the second range. As an additional example, at least one of the first range and the second range may be predetermined or dynamically calculated based on a location of the one or more targets.

In further aspects of the disclosure, the processor is configured to cause further aspects and features to be displayed in the view. In an aspect, the processor is configured to determine intensity associated with the one or more targets and cause the intensity associated with the target to be displayed. Additionally, the one or more targets may be displayed in a maximal surface size in the view.

In an aspect, the processor is further configured to cause one or more markings to be displayed, for example overlaid, on the one or more targets and to cause a crosshair to be displayed in the view to assist alignment to a center of the one or more targets.

In yet another aspect of the disclosure a system for navigating to a target is provided. The system includes an electromagnetic tracking system having electromagnetic tracking coordinates, a catheter configured to couple to the electromagnetic tracking system, and a computing device configured to operably coupled to the electromagnetic tracking system and the catheter. The catheter includes a location sensor for detecting a location of the catheter in the electromagnetic tracking coordinates. The computing device is configured to generate a three-dimensional (3D) rendering of a patient's airways, and generate a 3D view by executing a first transfer function for a first range from the location of the catheter to identify one or more airways within the 3D rendering and executing a second transfer function for a second range from the location of the catheter to identify one or more targets within the 3D rendering. In an aspect, the computing device is configured to display the generated 3D view.

In an aspect, the catheter further includes and a pose sensor for detecting a pose of the catheter in the electromagnetic tracking coordinates.

In an aspect, at least one of the first range or the second range is dynamically calculated based on the location of the catheter relative to the target.

In an aspect, the first range is less than the second range.

In an aspect, the computing device is configured to determine whether a number of the one or more airways within the 3D rendering exceeds a threshold, and execute a modified transfer function to identify one or more airways within the 3D rendering when it is determined that the number of the one or more airways within the 3D rendering does not exceed the threshold. The modified transfer function may include at least one of a modified filtering threshold, a modified accumulation of voxels, or a modified projection range.

In yet another aspect of the disclosure, a method for navigating to a target is provided. The method includes generating a three-dimensional (3D) rendering of a patient's lungs, executing a first transfer function for a first range from a location of a probe within the patient's lungs to identify one or more airways within the 3D rendering, executing a second transfer function for a second range from the location of the probe to identify one or more targets within the 3D rendering, and generating a 3D view based on the first transfer function and the second transfer function.

In an aspect, the method further includes displaying the 3D view.

In an aspect, the first range is less than the second range.

In an aspect, the method further includes determining whether a number of the one or more airways within the 3D rendering exceeds a threshold and executing a modified transfer function to identify one or more airways within the 3D rendering when it is determined that the number of the one or more airways within the 3D rendering does not exceed the threshold. In an aspect, executing the modified transfer function includes at least one of modifying a filtering threshold, modifying an accumulation of voxels, or modifying a projection range.

Any of the above aspects and embodiments of the disclosure may be combined without departing from the scope of the disclosure.

BRIEF DESCRIPTION OF THE DRAWINGS

Various aspects and features of the disclosure are described hereinbelow with references to the drawings, wherein.

DETAILED DESCRIPTION

Figure 1:
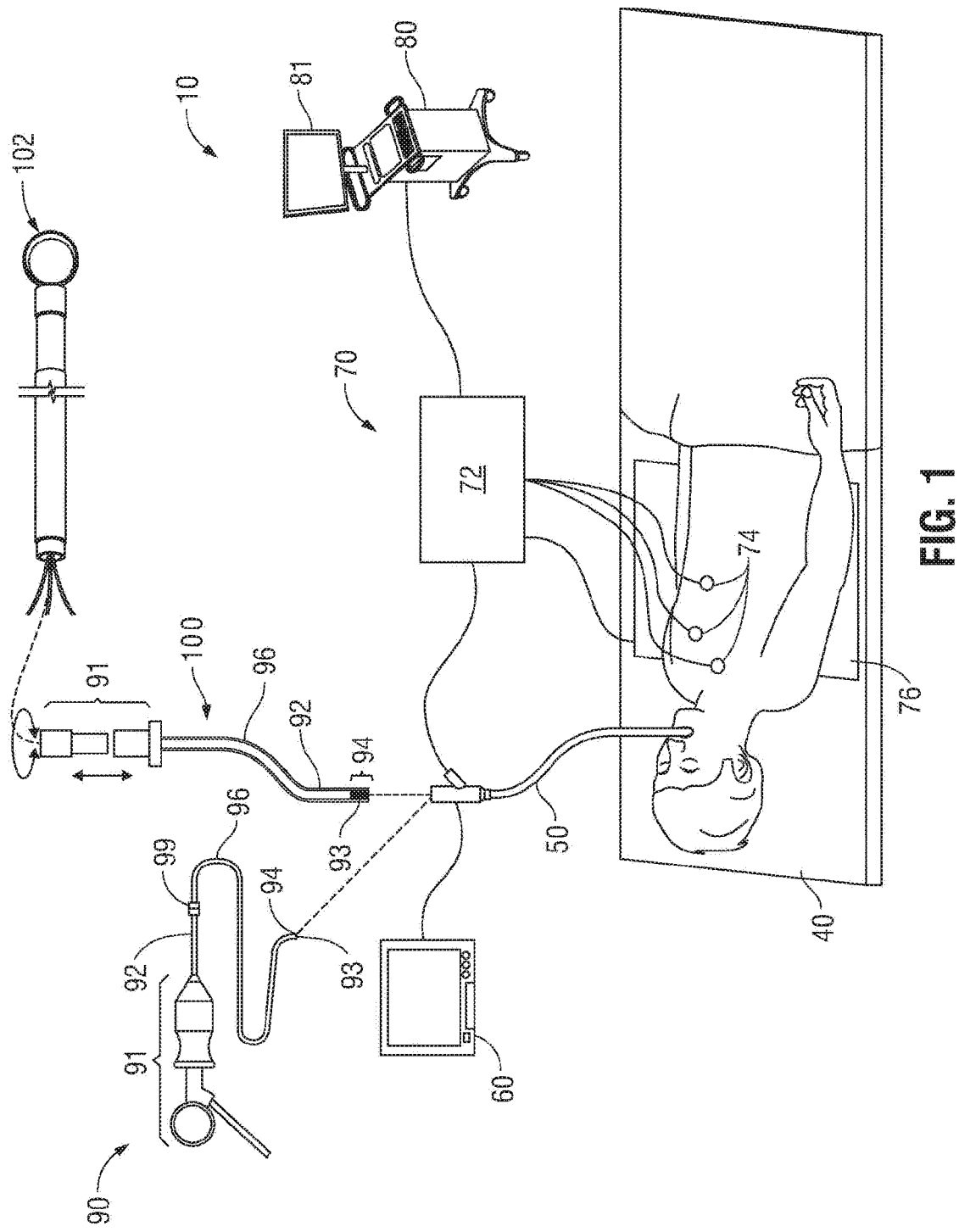
FIG. 1 is a perspective view of an electromagnetic navigation system in accordance with the disclosure.

The disclosure relates to systems and methods for internally guided navigation of catheters based on a model generated from CT image data.

In the past, scanned two-dimensional (2D) images of the lungs have been used to aid in visualization. In order to obtain the 2D images, a patient undergoes a CT scans. In addition to using scanned 2D images, three-dimensional (3D) models may also be used to virtually navigate through the body. The use of 3D models for navigation is more complex than using 2D images and includes several challenges. One challenge involves guiding a catheter to the target in 3D. Many views have been developed, some of them using cross-sections, and a proposed view is designed to assist with guidance. However, when one tries to look through the whole volume from a point of view instead of looking at a cross-section, the view may be obstructed and objects, which are behind other objects, might not be seen. Methods have been developed to alleviate the obstructed view problem, such as adding transparency to some of the volume or highlighting farther objects. One of the known methods involves Maximum Intensity Projection (MIP) which is a volume rendering method for 3D data that projects in the visualization plane the voxels with maximum intensity that fall in the way of parallel rays traced from the viewpoint to the plane of projection.

However, when using MIP to align an electromagnetic navigation catheter towards a lesion, traditional methods may result in lesions located beyond objects, such as bones or other non-soft tissue, not being visible. Therefore, there is a need to develop new view development techniques that improve upon MIP.

The disclosure is related to devices, systems, and methods for internally guided navigation of catheters based on a model generated from CT image data to guide a catheter to a target. In the disclosure, the system provides a view of a defined section of a volume from the perspective of the catheter. To achieve the view disclosed in the current application, two filters are separately applied to a rendered 3D volume. The filters isolate airway tissue and lesion tissue from the 3D rendering so that it can be combined in order to generate a view which presents only airways and lesions and eliminates obstacles such as bones which would ordinarily obscure a view from the catheter.

Alignment of catheter 102 may be a necessary component of pathway planning for performing an ELECTROMAGNETIC NAVIGATION BRONCHOSCOPY® (ENB) procedure using an electromagnetic navigation (EMN) system. An ENB procedure generally involves at least two phases: (1) planning a pathway to a target located within, or adjacent to, the patient's lungs; and (2) navigating a probe to the target along the planned pathway. These phases are generally referred to as (1) "planning" and (2) "navigation." The planning phase of an ENB procedure is more fully described in commonly-owned U.S. Pat. Nos. 9,459,770; and 9,639,666 and U.S. Patent Publication No. 2014/0270441, all entitled "Pathway Planning System and Method," filed on Mar. 15, 2013, by Baker, the entire contents of which are hereby incorporated by reference. An example of the navigation software can be found in commonly assigned U.S. Patent Publication No. 2016/0000302 entitled "SYSTEM AND METHOD FOR NAVIGATING WITHIN THE LUNG" the entire contents of which are incorporated herein by reference.

Prior to the planning phase, the patient's lungs are imaged by, for example, a computed tomography (CT) scan, although additional applicable methods of imaging will be known to those skilled in the art. The image data assembled during the CT scan may then be stored in, for example, the Digital Imaging and Communications in Medicine (DICOM) format, although additional applicable formats will be known to those skilled in the art. The CT scan image data may then be loaded into a planning software application ("application") to be used during the planning phase of the ENB procedure.

Embodiments of the systems and methods are described with reference to the accompanying drawings. Like reference numerals may refer to similar or identical elements throughout the description of the figures. This description may use the phrases "in an embodiment," "in embodiments," "in some embodiments," or "in other embodiments," which may each refer to one or more of the same or different embodiments in accordance with the disclosure.

FIG. 1 illustrates an electromagnetic navigation (EMN) system 10 in accordance with the disclosure. Among other tasks that may be performed using the EMN system 10 are planning a pathway to target tissue, navigating a positioning assembly to the target tissue, navigating a catheter 102 to the target tissue to obtain a tissue sample from the target tissue using catheter 102, and digitally marking the location where the tissue sample was obtained, and placing one or more echogenic markers at or around the target.

EMN system 10 generally includes an operating table 40 configured to support a patient; a bronchoscope 50 configured for insertion through the patient's mouth and/or nose into the patient's airways; monitoring equipment 60 coupled to bronchoscope 50 for displaying video images received from bronchoscope 50; a tracking system 70 including a tracking module 72, a plurality of reference sensors 74, and an electromagnetic field generator 76; a workstation 80 including software and/or hardware used to facilitate pathway planning, identification of target tissue, navigation to target tissue, and digitally marking the biopsy location FIG. 1 also depicts two types of catheter guide assemblies 90, 100. Both catheter guide assemblies 90, 100 are usable with the EMN system 10 and share a number of common components. Each catheter guide assembly 90, 100 includes a handle 91, which is connected to an extended working channel (EWC) 96. The EWC 96 is sized for placement into the working channel of a bronchoscope 50. In operation, a locatable guide (LG) 92, including an electromagnetic (EM) sensor 94, is inserted into the EWC 96 and locked into position such that the sensor 94 extends a desired distance beyond the distal tip 93 of the EWC 96. The location of the EM sensor 94, and thus the distal end of the EWC 96, within an electromagnetic field generated by the electromagnetic field generator 76 can be derived by the tracking module 72, and workstation 80.

Figure 2:
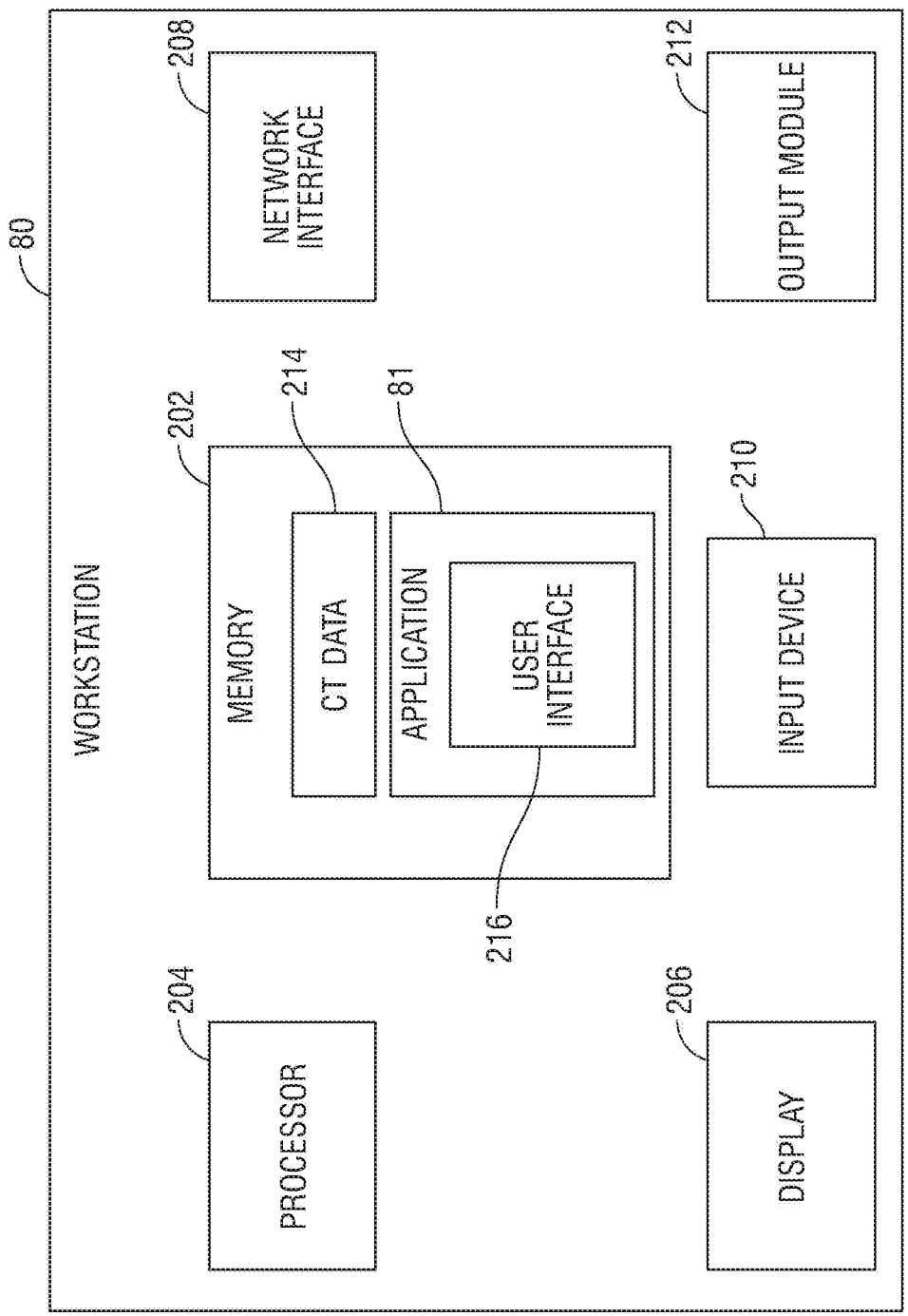
FIG. 2 is a schematic diagram of a workstation configured for use with the system of FIG. 1.

FIG. 2 illustrates a system diagram of workstation 80. Workstation 80 may include memory 202, processor 204, display 206, network interface 208, input device 210, and/or output module 212. Workstation 80 implements the methods that will be described herein.

Figure 3:
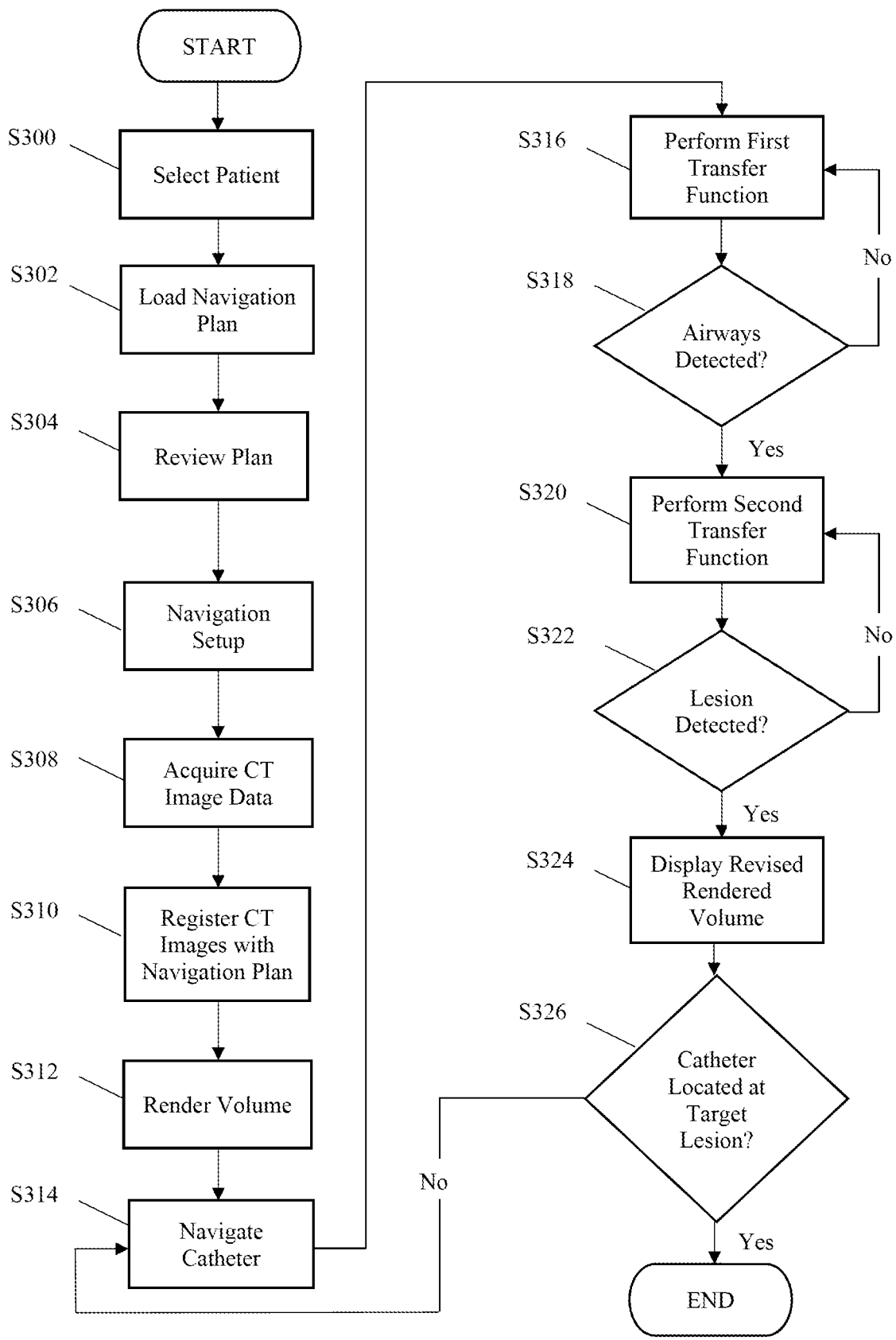
FIG. 3 is a flow chart illustrating a method of navigation in accordance with an embodiment of the disclosure.

FIG. 3 depicts a method of navigation using the navigation workstation 80 and the user interface 216. At step S300 user interface 216 presents the clinician with a view (not shown) for the selection of a patient. The clinician may enter patient information such as, for example, the patient name or patient ID number, into a text box to select a patient on which to perform a navigation procedure. Alternatively, the patient may be selected from a drop down menu or other similar methods of patient selection. Once the patient has been selected, the user interface 216 presents the clinician with a view (not shown) including a list of available navigation plans for the selected patient. At step S302, the clinician may load one of the navigation plans by activating the navigation plan. The navigation plans may be imported from a procedure planning software and include CT images of the selected patient.

Once the patient has been selected and a corresponding navigation plan has been loaded, the user interface 216 presents the clinician with a patient details view (not shown) At step S304 which allows the clinician to review the selected patient and plan details. Examples of patient details presented to the clinician in the timeout view may include the patient's name, patient ID number, and birth date. Examples of plan details include navigation plan details, automatic registration status, and/or manual registration status. For example, the clinician may activate the navigation plan details to review the navigation plan, and may verify the availability of automatic registration and/or manual registration. The clinician may also activate an edit button edit the loaded navigation plan from the patient details view. Activating the edit button of the loaded navigation plan may also activate the planning software described above. Once the clinician is satisfied that the patient and plan details are correct, the clinician proceeds to navigation setup at step S306. Alternatively, medical staff may perform the navigation setup prior to or concurrently with the clinician selecting the patient and navigation plan.

During navigation setup at step S306, the clinician or other medical staff prepares the patient and operating table by positioning the patient on the operating table over the electromagnetic field generator 76. The clinician or other medical staff position reference sensors 74 on the patient's chest and verify that the sensors are properly positioned, for example, through the use of a setup view presented to the clinician or other medical staff by user interface 216. Setup view may, for example, provide the clinician or other medical staff with an indication of where the reference sensors 74 are located relative to the magnetic field generated by the electromagnetic field generator 76. Patient sensors allow the navigation system to compensate for patient breathing cycles during navigation. The clinician also prepares LG 92, EWC 96, and bronchoscope 50 for the procedure by inserting LG 92 into EWC 96 and inserting both LG 92 and EWC 96 into the working channel of bronchoscope 50 such that distal tip 93 of LG 92 extends from the distal end of the working channel of bronchoscope 50. For example, the clinician may extend the distal tip 93 of LG 92 10 mm beyond the distal end of the working channel of bronchoscope 50.

Figure 4:
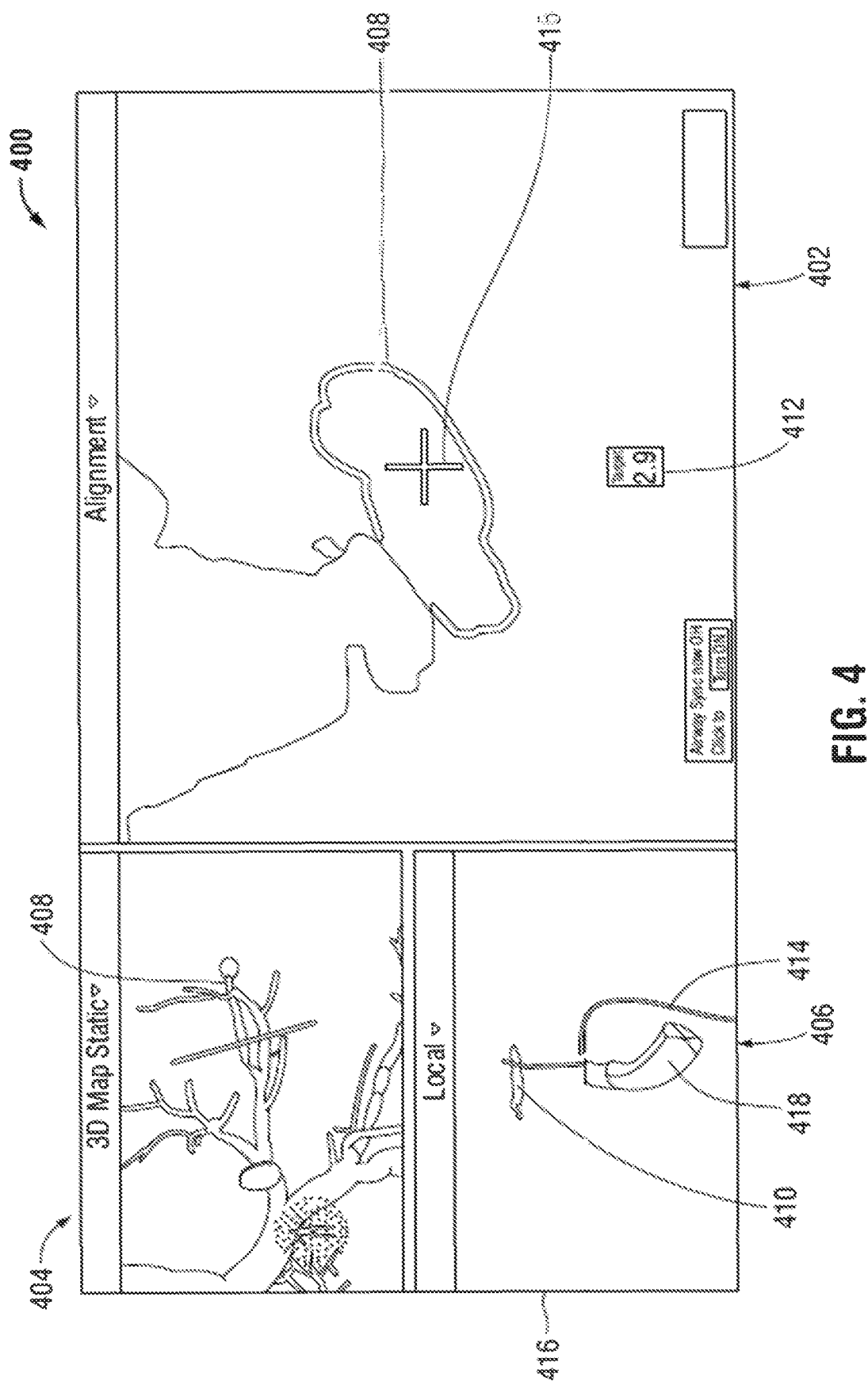
FIG. 4 is an illustration of a user interface of the workstation of FIG. 2 presenting a view for performing registration in accordance with the disclosure.

Once setup is complete, workstation 80 presents a view 400, as shown in FIG. 4, via the user interface 216. CT image data is acquired and displayed at step 308. At step 310, the CT image data is registered with the selected navigation plan. An example method for registering images with a navigation plan is described in the aforementioned U.S. Patent Publication No. 2016/0000302.

At step S312, workstation 80 performs a volume rendering algorithm based on the CT image data included in the navigation plan and position signals from sensor 94 to generate a 3D view 404 of the walls of the patient's airways as shown in FIG. 4. The 3D view 404 uses a perspective rendering that supports perception of advancement when moving closer to objects in the volume. The 3D view 404 also presents the user with a navigation pathway providing an indication of the direction along which the user will need to travel to reach the lesion 410. The navigation pathway may be presented in a color or shape that contrasts with the 3D rendering so that the user may easily determine the desired path to travel. Workstation 80 also presents a local view 406 as shown in FIG. 4 that includes a slice of the 3D volume located at and aligned with the distal tip 93 of LG 92. Local view 406 shows the lesion 410 and the navigation pathway 414 overlaid on slice 416 from an elevated perspective. The slice 416 that is presented by local view 406 changes based on the location of EM sensor 94 relative to the 3D volume of the loaded navigation plan. Local view 406 also presents the user with a virtual representation of the distal tip 93 of LG 92 in the form of a virtual probe 418. The virtual probe 418 provides the user with an indication of the direction that distal tip 93 of LG 92 is facing so that the user can control the advancement of the LG 92 in the patient's airways.

At step S314, catheter 102 is navigated through the airways. Catheter 102 may be navigated through catheter guide assemblies 90, 100 until catheter 102 approaches the target. Alternatively, catheter 102 may be navigated independently of catheter guide assemblies 90, 100. Catheter 102 is navigated via manipulation of handle 91 which can be manipulated by rotation and compression. Once catheter 102 is located approximate the target, steps S314-S316 begin in order to render a 3D volume including locations of one or more airways and one or more targets. Until catheter 102 is located at the target, catheter 102 is further navigated, at step S314, using the 3D volume and locations of one or more airways and one or more targets continually generated in steps S314-S316.

At steps S316 and S320, a view including lungs and lesions is rendered by projecting, from the location and orientation (i.e., the perspective) of catheter 102, parallel beams which accumulate densities until they encounter an opaque object (e.g., bone). The volume rendering is performed in two steps: 1) collecting voxel data and 2) accumulating the voxel data in the direction of the beams, which is projected from the location and orientation of catheter 102, until the beam is stopped, at which point the voxel data is added together.

Further at step S316, workstation 80 applies a first transfer function to the volume rendered at step S314. The first transfer function is applied to a limited range projected from the position of catheter 102. The limited range may be predefined or be dynamically calculated based on a location of and/or distance to the target. Along the limited range projected from the position of catheter 102, the first transfer function accumulates voxels which have a density and/or a color within a certain range indicating that the pixel represents a wall of a patient's airways. As a result of applying the first transfer function, workstation 80 generates a filtered volume rendering preferably showing the patient's airways.

Further at step S318, workstation 80 assesses the result of applying the first transfer function to the rendered volume. Workstation 80 may use, for example, image recognition software to determine whether recognizable, airway-shaped elements are visible in the filtered volume rendering. Alternatively, the filtered volume rendering may be presented to the clinician such that the clinician may inspect the filtered volume rendering and determine whether airways are visible. The clinician may then indicate on the user interface whether airways are visible. If either workstation 80 or the clinician determines that airways are not visible, the process returns to step S316 wherein the first transfer function is re-applied to the volume rendering with a modified filtering threshold, a modified accumulation of voxels, or a modified projection range. If, at step S316, either workstation 80 or the clinician determines that a requisite number of airways are visible, the process proceeds to step S320.

At step S320, workstation 80 applies a second transfer function to the volume rendered at step S314. The second transfer function is applied to an unlimited range projected from the position of catheter 102. Though, as a practical matter, it is likely that the projected range will be limited by the size of the rendered volume. The second transfer function may also be applied to a limited range projected from the position of catheter 102. Along the range projected from the position of catheter 102, the second transfer function accumulates voxels which have a density and/or a color within a certain range indicating that the pixel represents a target tissue such as a lesion. Applying the second transfer function to an unlimited range from the position of catheter 102 allows voxels representing target tissue such as a lesion to be detected and shown beyond opaque objects (e.g., bones). As a result of applying the second transfer function to the rendered volume, workstation 80 generates a filtered volume rendering preferably showing target tissues, including those located beyond bones and other opaque objects.

At steps S322, workstation 80 assesses the result of applying the second transfer function to the rendered volume. Workstation 80 may use, for example, image recognition software to determine whether recognizable, airway-shaped elements are visible in the filtered volume rendering. Alternatively, the filtered volume rendering may be presented to the clinician such that the clinician may inspect the filtered volume rendering and determine whether airways are visible. The clinician may then indicate on the user interface whether target tissue is visible. If either workstation 80 or the clinician determines that target tissue is not visible, the process returns to step S320 wherein the second transfer function is re-applied to the volume rendering with a modified filtering threshold, a modified accumulation of voxels, or a modified projection range. If, at step S322, either workstation 80 or the clinician determines that a target tissue is visible, the process proceeds to step S324.

Limiting the transfer functions to highlighted structures within the limited range of the distal tip 93 may reduce the load on processor 204. By using a limited range, denser structures that may obscure the lesion may be omitted permitting the lesion to be displayed. The second transfer function may be configured to cause lesions within the range to be displayed in their maximal surface size permitting the user to aim for the center of the target. As shown in alignment view 402, the second transfer functions may be tuned to highlight lesion-density tissue and filter out most other densities in the CT volume, creating a clearer picture in which lung lesions stand out over dark background. A marking 408, e.g., a sphere or ellipsoid, may be used to represent the planned target and is overlaid on the rendered volume to reduce risk of aligning to the wrong object. A crosshair 415 in the center of the view assists the user in aligning distal tip 93 with the center of the target. The distance 412 from the distal tip 93 to the center of the marked target is displayed next to the crosshair 415, permitting the user to find the best balance between alignment and proximity At step S324, the filtered volume rendering generated by applying the first transfer function and the filtered volume rendering generated by applying the second transfer function are combined in order to generate a display showing the patient's airways and target tissue. An example displays resulting from the combination are shown at FIG. 4.

At step S326, the clinician or workstation 80 determines whether the catheter is a located at the target. If the catheter is not located at the target, the process returns to step S314 wherein the clinician continues to navigate the catheter toward the target. As the catheter is navigated toward the target, the display volume is continually rendering and the first and the second transfer functions are applied to generate a view showing airways and the target.

In the embodiments, the alignment of catheter 102 using CT image data and 3D models permits a better aiming experience over other CT volume representations. Target areas of lesions may be shown from a distance, where a normal CT slice would not be useful. The embodiments permit a user to assess optimal balance between alignment/proximity, which defines the best location for catheter introduction. The view looks similar to CT images thereby assuring clinicians that the information they are looking at is real, permits aiming to various parts of the lesion structure, and assures users that they are at the planned target. In the 3D models, irrelevant structures in the range are reduced or eliminated, permitting the user to clearly identify the target.

FIG. 4 shows 3D view 404 which show walls of the patient's airways. The 3D view 404 uses a perspective rendering that supports perception of advancement when moving closer to objects in the volume. The 3D view 404 also presents the user with a navigation pathway providing an indication of the direction along which the user will need to travel to reach the lesion 410. The navigation pathway may be presented in a color or shape that contrasts with the 3D rendering so that the user may easily determine the desired path to travel. Workstation 80 also presents a local view 406 as shown in FIG. 4 that includes a slice of the 3D volume located at and aligned with the distal tip 93 of LG 92. Local view 406 shows the lesion 410 and the navigation pathway 414 overlaid on slice 416 from an elevated perspective. The slice 416 that is presented by local view 406 changes based on the location of EM sensor 94 relative to the 3D volume of the loaded navigation plan. Local view 406 also presents the user with a virtual representation of the distal tip 93 of LG 92 in the form of a virtual probe 418. The virtual probe 418 provides the user with an indication of the direction that distal tip 93 of LG 92 is facing so that the user can control the advancement of the LG 92 in the patient's airways.

Referring back to FIG. 1, catheter guide assemblies 90, 100 have different operating mechanisms, but each contain a handle 91 that can be manipulated by rotation and compression to steer the distal tip 93 of the LG 92, extended working channel 96. Catheter guide assemblies 90 are currently marketed and sold by Covidien LP under the name SUPERDIMENSION® Procedure Kits, similarly catheter guide assemblies 100 are currently sold by Covidien LP under the name EDGE™ Procedure Kits, both kits include a handle 91, extended working channel 96, and locatable guide 92. For a more detailed description of the catheter guide assemblies 90, 100 reference is made to commonly-owned U.S. patent application Ser. No. 13/836,203 filed on Mar. 15, 2013 by Ladtkow et al., the entire contents of which are hereby incorporated by reference.

In FIG. 1, the patient is shown lying on operating table 40 with bronchoscope 50 inserted through the patient's mouth and into the patient's airways. Bronchoscope 50 includes a source of illumination and a video imaging system (not explicitly shown) and is coupled to monitoring equipment 60, e.g., a video display, for displaying the video images received from the video imaging system of bronchoscope 50.

Catheter guide assemblies 90, 100 including LG 92 and EWC 96 are configured for insertion through a working channel of bronchoscope 50 into the patient's airways (although the catheter guide assemblies 90, 100 may alternatively be used without bronchoscope 50). The LG 92 and EWC 96 are selectively lockable relative to one another via a locking mechanism 99. A six degrees-of-freedom electromagnetic tracking system 70, e.g., similar to those disclosed in U.S. Pat. No. 6,188,355 and published PCT Application Nos. WO 00/10456 and WO 01/67035, the entire contents of each of which is incorporated herein by reference, or any other suitable positioning measuring system, is utilized for performing navigation, although other configurations are also contemplated. Tracking system 70 is configured for use with catheter guide assemblies 90, 100 to track the position of the EM sensor 94 as it moves in conjunction with the EWC 96 through the airways of the patient, as detailed below.

As shown in FIG. 1, electromagnetic field generator 76 is positioned beneath the patient. Electromagnetic field generator 76 and the plurality of reference sensors 74 are interconnected with tracking module 72, which derives the location of each reference sensor 74 in six degrees of freedom. One or more of reference sensors 74 are attached to the chest of the patient. The six degrees of freedom coordinates of reference sensors 74 are sent to workstation 80, which includes application 81 where sensors 74 are used to calculate a patient coordinate frame of reference.

Also shown in FIG. 1 is a catheter 102 which is insertable into the catheter guide assemblies 90, 100 following navigation to a target and removal of the LG 92. The catheter 102 is used to collect one or more tissue sample from the target tissue. As detailed below, catheter 102 is further configured for use in conjunction with tracking system 70 to facilitate navigation of catheter 102 to the target tissue, tracking of a location of catheter 102 as it is manipulated relative to the target tissue to obtain the tissue sample, and/or marking the location where the tissue sample was obtained.

Although navigation is detailed above with respect to EM sensor 94 being included in the LG 92 it is also envisioned that EM sensor 94 may be embedded or incorporated within catheter 102 where catheter 102 may alternatively be utilized for navigation without need of the LG or the necessary tool exchanges that use of the LG requires. A variety of useable catheters are described in U.S. Patent Publication Nos. 2015/0141869 and 2015/0141809 both entitled DEVICES, SYSTEMS, AND METHODS FOR NAVIGATING A CATHETER TO A TARGET LOCATION AND OBTAINING A TISSUE SAMPLE USING THE SAME, filed Nov. 20, 2013 and U.S. Patent Publication No. 2015/0265257 having the same title and filed Mar. 14, 2014, the entire contents of each of which are incorporated herein by reference and useable with the EMN system 10 as described herein.

During procedure planning, workstation 80 utilizes computed tomographic (CT) image data for generating and viewing a three-dimensional model ("3D model") of the patient's airways, enables the identification of target tissue on the 3D model (automatically, semi-automatically or manually), and allows for the selection of a pathway through the patient's airways to the target tissue. More specifically, the CT scans are processed and assembled into a 3D volume, which is then utilized to generate the 3D model of the patient's airways. The 3D model may be presented on a display monitor 81 associated with workstation 80, or in any other suitable fashion. Using workstation 80, various slices of the 3D volume and views of the 3D model may be presented and/or may be manipulated by a clinician to facilitate identification of a target and selection of a suitable pathway through the patient's airways to access the target. The 3D model may also show marks of the locations where previous biopsies were performed, including the dates, times, and other identifying information regarding the tissue samples obtained. These marks may also be selected as the target to which a pathway can be planned. Once selected, the pathway is saved for use during the navigation procedure. An example of a suitable pathway planning system and method is described in the aforementioned U.S. Pat. Nos. 9,459,770; and 9,639,666 and U.S. Patent Publication No. 2014/0270441.

During navigation, EM sensor 94, in conjunction with tracking system 70, enables tracking of EM sensor 94 and/or catheter 102 as EM sensor 94 or catheter 102 is advanced through the patient's airways.

Referring back to FIG. 2, memory 202 includes any non-transitory computer-readable storage media for storing data and/or software that is executable by processor 204 and which controls the operation of workstation 80. In an embodiment, memory 202 may include one or more solid-state storage devices such as flash memory chips. Alternatively or in addition to the one or more solid-state storage devices, memory 202 may include one or more mass storage devices connected to the processor 204 through a mass storage controller (not shown) and a communications bus (not shown). Although the description of computer-readable media contained herein refers to a solid-state storage, it should be appreciated by those skilled in the art that computer-readable storage media can be any available media that can be accessed by the processor 204. That is, computer readable storage media includes non-transitory, volatile and non-volatile, removable and non-removable media implemented in any method or technology for storage of information such as computer-readable instructions, data structures, program modules or other data. For example, computer-readable storage media includes RAM, ROM, EPROM, EEPROM, flash memory or other solid state memory technology, CD-ROM, DVD, Blu-Ray or other optical storage, magnetic cassettes, magnetic tape, magnetic disk storage or other magnetic storage devices, or any other medium which can be used to store the desired information and which can be accessed by workstation 80.

Memory 202 may store application 81 and/or CT data 214. Application 81 may, when executed by processor 204, cause display 206 to present user interface 216. Network interface 208 may be configured to connect to a network such as a local area network (LAN) consisting of a wired network and/or a wireless network, a wide area network (WAN), a wireless mobile network, a Bluetooth network, and/or the internet. Input device 210 may be any device by means of which a user may interact with workstation 80, such as, for example, a mouse, keyboard, foot pedal, touch screen, and/or voice interface. Output module 212 may include any connectivity port or bus, such as, for example, parallel ports, serial ports, universal serial busses (USB), or any other similar connectivity port known to those skilled in the art.

Any of the described methods, programs, algorithms or codes may be converted to, or expressed in, a programming language or computer program. A "Programming Language" and "Computer Program" is any language used to specify instructions to a computer, and includes (but is not limited to) these languages and their derivatives: Assembler, Basic, Batch files, BCPL, C, C+, C++, Delphi, Fortran, Java, JavaScript, Machine code, operating system command languages, Pascal, Perl, PL1, scripting languages, Visual Basic, metalanguages which themselves specify programs, and all first, second, third, fourth, and fifth generation computer languages. Also included are database and other data schemas, and any other meta-languages. For the purposes of this definition, no distinction is made between languages which are interpreted, compiled, or use both compiled and interpreted approaches. For the purposes of this definition, no distinction is made between compiled and source versions of a program. Thus, reference to a program, where the programming language could exist in more than one state (such as source, compiled, object, or linked) is a reference to any and all such states. The definition also encompasses the actual instructions and the intent of those instructions.

Although embodiments have been described in detail with reference to the accompanying drawings for the purpose of illustration and description, it is to be understood that the inventive processes and apparatus are not to be construed as limited thereby. It will be apparent to those of ordinary skill in the art that various modifications to the foregoing embodiments may be made without departing from the scope of the disclosure.

What is claimed is:

1. A system for navigating to a target, the system comprising:
   a probe configured to be navigated through a patient's airways, the probe including a location sensor and a pose sensor, the location sensor configured to generate location information of the probe and the pose sensor configured to generate pose information of the probe; and
   a workstation in operative communication with the probe, the workstation including a memory and at least one processor, the memory storing a navigation plan and a program that, when executed by the processor, is configured to:
   generate a three-dimensional (3D) rendering of the patient's airways;
   receive the location information and the pose information;
   generate a view using the 3D rendering by executing a first transfer function for a first range from the location sensor to identify one or more airways within the 3D rendering and executing a second transfer function for a second range from the location sensor to identify one or more targets within the 3D rendering, the second transfer function configured to distinguish between a density of the one or more targets and a density of structures other than the one or more targets; and
   cause the view to be displayed featuring the identified one or more airways, the identified one or more targets, and at least a portion of the navigation plan, wherein the second transfer function causes the displayed view to omit structures other than the one or more targets located beyond the range of the first transfer function to avoid obscuring the view of the one or more targets within the 3D rendering based upon the differing densities of the one or more targets and the structures other than the one or more targets.

2. The system according to claim 1, wherein the first transfer function is executed using a first voxel density, and the second transfer function is executed using a second voxel density.

3. The system according to claim 1, wherein the first range is less than the second range.

4. The system according to claim 1, wherein at least one of the first range and the second range is predetermined.

5. The system according to claim 1, wherein at least one of the first range and the second range is dynamically calculated based on a location of the one or more targets.

6. The system according to claim 1, wherein the one or more targets include one or more lesions.

7. The system according to claim 1, wherein the view includes a mark overlaid on the one or more targets.

8. The system according to claim 1, wherein the view includes a crosshair to assist alignment to a center of the one or more targets.

9. A system for navigating to a target, the system comprising:
   an electromagnetic tracking system having electromagnetic tracking coordinates;
   a catheter configured to couple to the electromagnetic tracking system, the catheter including a location sensor for detecting a location of the catheter in the electromagnetic tracking coordinates; and
   a computing device configured to operably couple to the electromagnetic tracking system and the catheter, the computing device configured to:
   generate a three-dimensional (3D) rendering of a patient's airways; and
   generate a 3D view by executing a first transfer function for a first range from the location of the catheter to identify one or more airways within the 3D rendering and executing a second transfer function for a second range from the location of the catheter to identify one or more targets within the 3D rendering, the second transfer function configured to distinguish between a density of the one or more targets and a density of structures other than the one or more targets,
   wherein the second transfer function causes the generated 3D view to omit structures other than the one or more targets located beyond the range of the first transfer function to avoid obscuring the view of the one or more targets within the 3D rendering based upon the differing densities of the one or more targets and the structures other than the one or more targets.

10. The system according to claim 9, wherein the catheter includes a pose sensor for detecting a pose of the catheter in the electromagnetic tracking coordinates.

11. The system according to claim 9, wherein the computing device is configured to display the generated 3D view featuring the identified one or more airways, the identified one or more targets, and at least a portion of a navigation plan.

12. The system according to claim 9, wherein at least one of the first range or the second range is dynamically calculated based on the location of the catheter relative to the target.

13. The system according to claim 9, wherein the first range is less than the second range.

14. The system according to claim 9, wherein the computing device is configured to:
   determine whether a number of the one or more airways within the 3D rendering exceeds a threshold; and execute a modified transfer function to identify one or more airways within the 3D rendering when it is determined that the number of the one or more airways within the 3D rendering does not exceed the threshold.

15. The system according to claim 14, wherein the modified transfer function includes at least one of a modified filtering threshold, a modified accumulation of voxels, or a modified projection range.

16. A method for navigating to a target, the method comprising:
    generating a three-dimensional (3D) rendering of a patient's lungs;
    executing a first transfer function for a first range from a location of a probe within the patient's lungs to identify one or more airways within the 3D rendering;
    executing a second transfer function for a second range from the location of the probe to identify one or more targets within the 3D rendering, the second transfer function configured to distinguish between a density of the one or more targets and a density of structures other than the one or more targets; and
    generating a 3D view based on the first transfer function and the second transfer function,
    wherein the second transfer function causes the generated 3D view to omit structures other than the one or more targets located beyond the range of the first transfer function to avoid obscuring the view of the one or more targets within the 3D rendering based upon the differing densities of the one or more targets and the structures other than the one or more targets.

17. The method according to claim 16, further comprising displaying the 3D view featuring the identified one or more airways, the identified one or more targets, and at least a portion of a navigation plan.

18. The method according to claim 16, wherein the first range is less than the second range.

19. The method according to claim 16, further comprising:
    determining whether a number of the one or more airways within the 3D rendering exceeds a threshold; and
    executing a modified transfer function to identify one or more airways within the 3D rendering when it is determined that the number of the one or more airways within the 3D rendering does not exceed the threshold.

20. The method according to claim 19, wherein executing the modified transfer function includes at least one or modifying a filtering threshold, modifying an accumulation of voxels, or modifying a projection range.

* * * * *